United States Patent [19]

Dudar et al.

[11] Patent Number: 5,100,394
[45] Date of Patent: Mar. 31, 1992

[54] PRE-SLIT INJECTION SITE

[75] Inventors: Thomas E. Dudar; Steven C. Jepson, both of Palatine; Robert P. Dobbie, Lincolnshire; Peter L. Graham, Gurnee; Michael J. Finley, Park City; Richard A. Rollins, Mundelein, all of Ill.

[73] Assignee: Baxter International Inc., Deerfield, Ill.

[21] Appl. No.: 425,790

[22] Filed: Oct. 23, 1989

Related U.S. Application Data

[63] Continuation-in-part of Ser. No. 147,414, Jan. 25, 1988, abandoned.

[51] Int. Cl.⁵ ............................................. A61M 25/00
[52] U.S. Cl. ..................................................... 604/283
[58] Field of Search ............... 604/239, 240, 241, 242, 604/243, 271, 272, 273, 274, 283, 405, 411, 412, 413, 414, 415, 416, 905, 84, 85, 86

[56] References Cited

U.S. PATENT DOCUMENTS

| | | |
|---|---|---|
| 3,376,866 | 4/1968 | Ogle . |
| 3,788,369 | 1/1974 | Killinger . |
| 3,976,073 | 8/1976 | Quick et al. . |
| 3,995,630 | 12/1976 | van de Veerdonk . |
| 4,411,662 | 10/1983 | Pearson . |
| 4,434,822 | 3/1984 | Bellamy et al. . |
| 4,583,971 | 4/1986 | Bocquet et al. . |
| 4,607,671 | 8/1986 | Aalto et al. . |
| 4,610,674 | 9/1986 | Suzuki et al. ........................ 604/282 |
| 4,624,667 | 11/1986 | Rutnarak . |
| 4,675,020 | 6/1987 | McPhee . |
| 4,759,756 | 7/1988 | Forman et al. . |
| 4,768,568 | 9/1988 | Fournier et al. . |
| 4,787,429 | 11/1988 | Valentini . |
| 4,834,149 | 5/1989 | Fournier et al. . |
| 4,886,495 | 12/1989 | Reynolds . |
| 4,969,883 | 11/1990 | Gilbert et al. . |

FOREIGN PATENT DOCUMENTS

| | | |
|---|---|---|
| 1037428 | 8/1978 | Canada . |
| 1043744 | 12/1978 | Canada . |
| 1215945 | 12/1986 | Canada . |
| 8812460 | 2/1989 | Fed. Rep. of Germany . |

Primary Examiner—C. Fred Rosenbaum
Assistant Examiner—William W. Lewis
Attorney, Agent, or Firm—Paul C. Flattery; Amy L. H. Rockwell; Paul E. Schaafsma

[57] ABSTRACT

A pre-slit injection site includes a housing with a flow path therethrough. A first end of the housing carries a pre-slit septum. A second end of the housing carries a coupling component to adapt the site to standard vials. The coupling component, a vial adapter, includes an adapter spike with openings allowing for the drainage of fluid in the vial through the spike and into the injection site. The vial adapter is provided with a skirt housing unit which protects the adapter spike in manufacturing and use. The skirt housing unit also provides features to lockingly engage the adapter with injection site to standard vials, despite dimensional variations in vial closures. Another embodiment of the coupling component is a spike having a barb feature capable of insertion into a standard vial or port and resisting disengagement.

A blunt cannula is usable with the injection site combined with the coupling components.

11 Claims, 11 Drawing Sheets

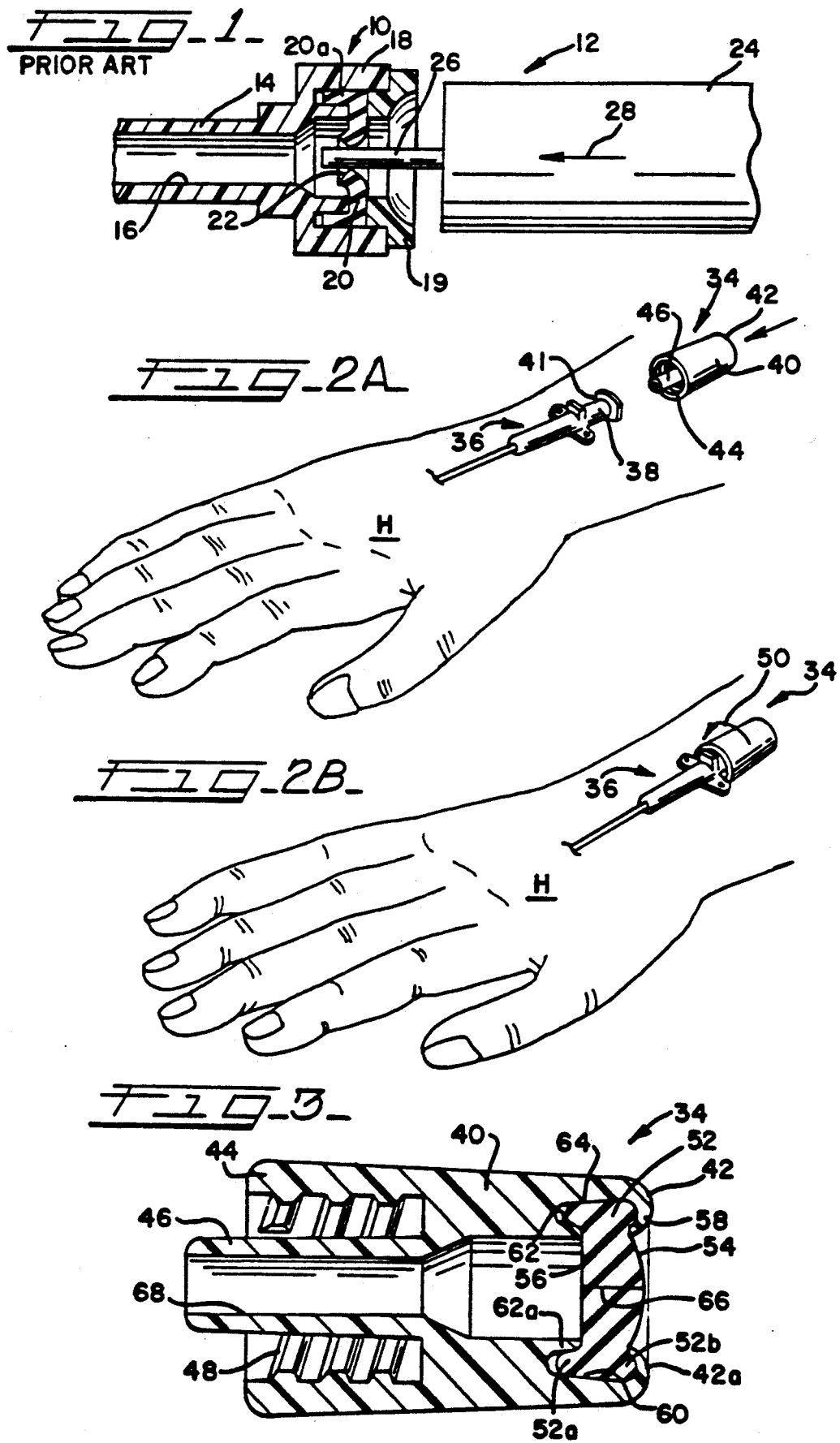

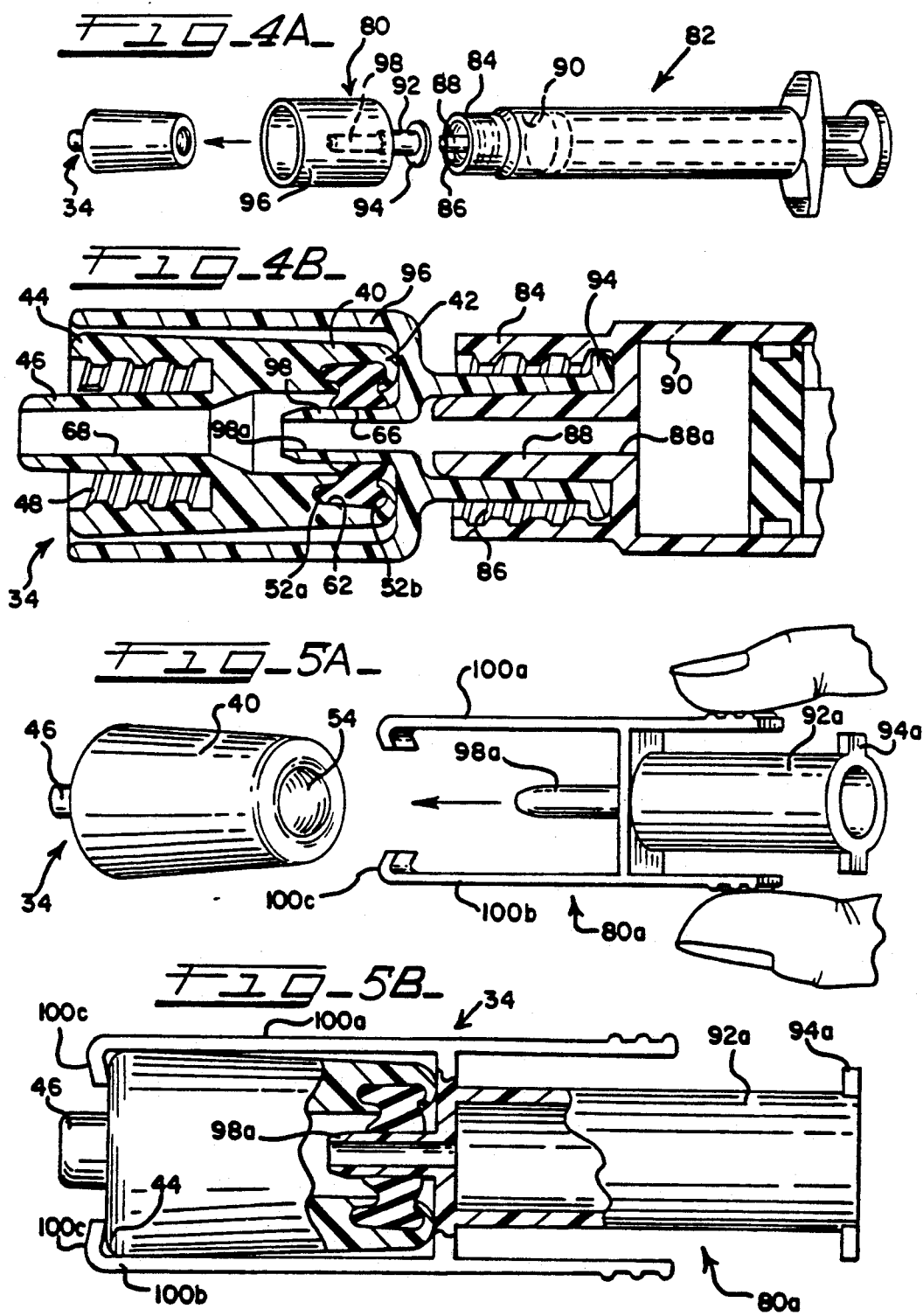

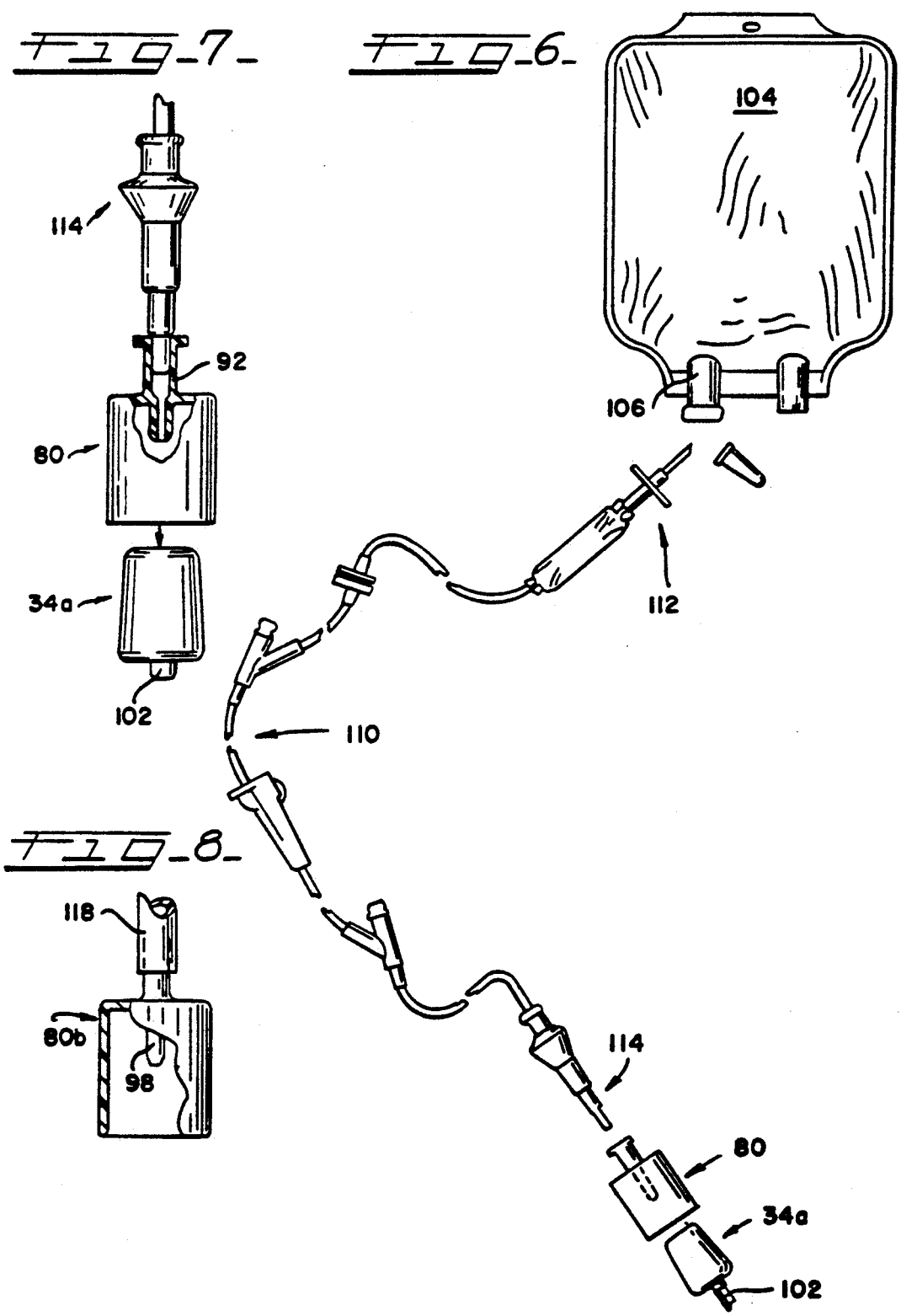

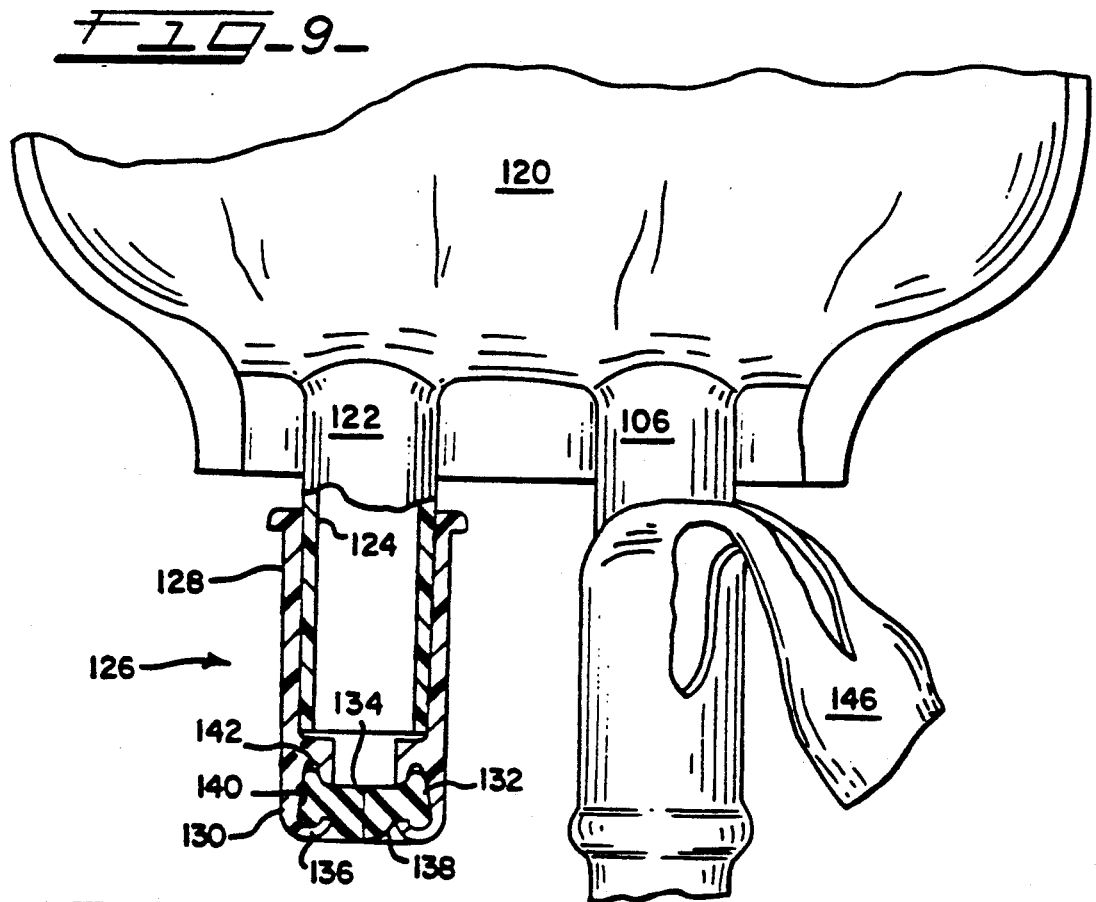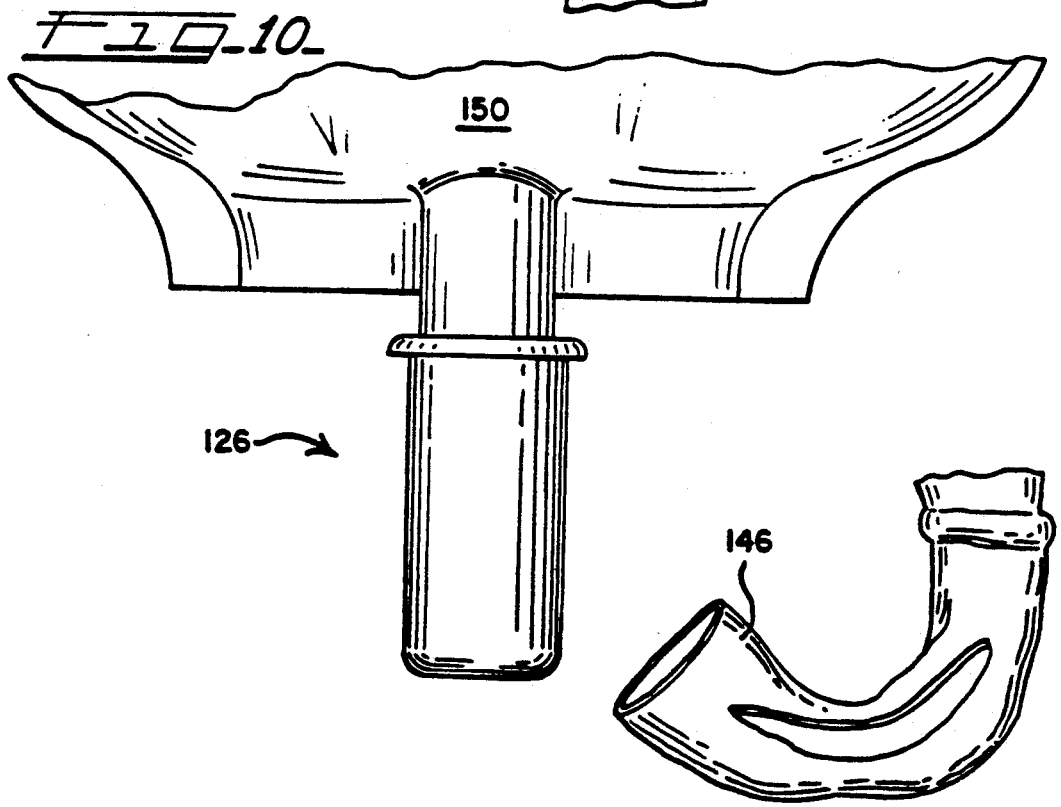

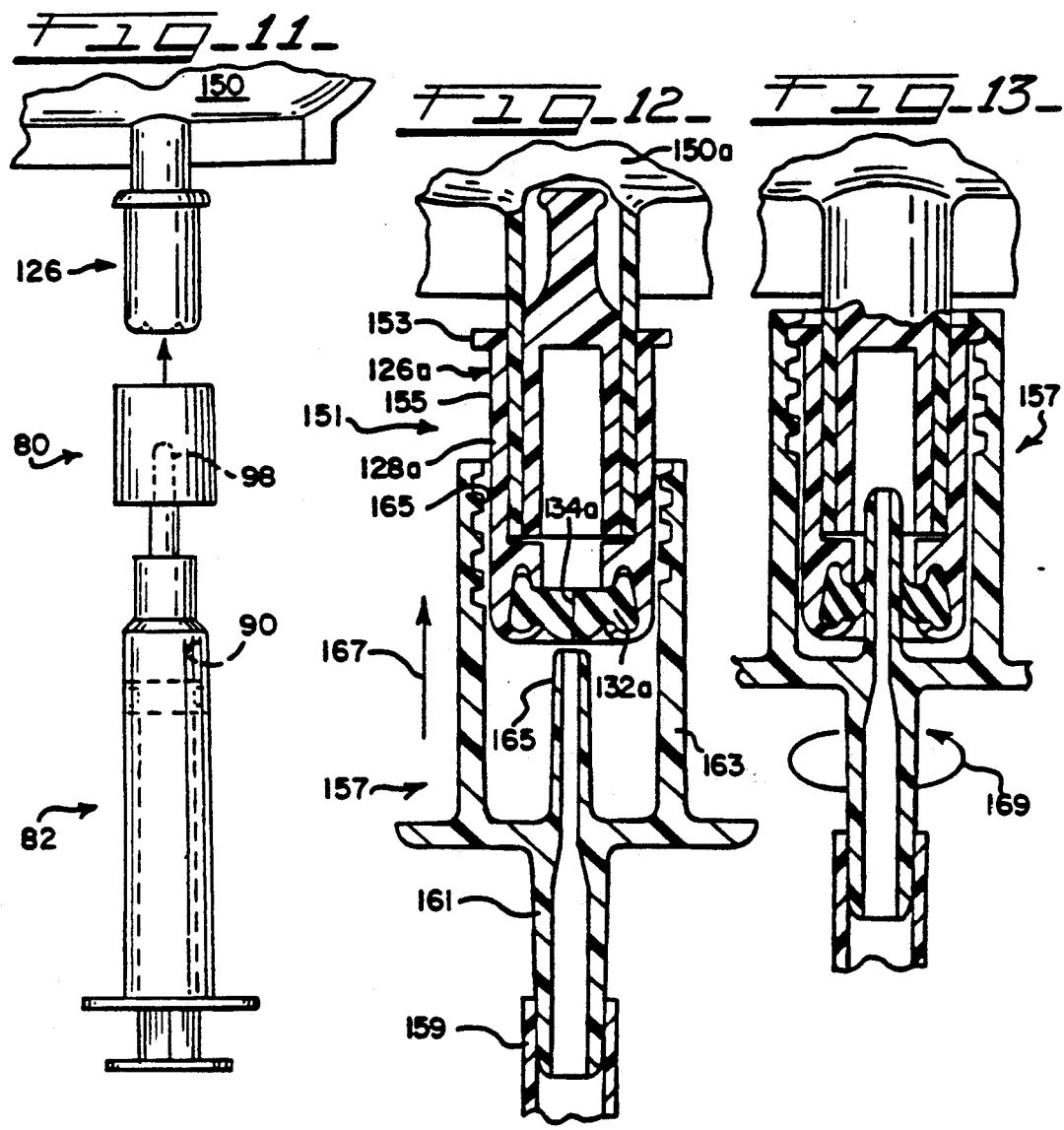
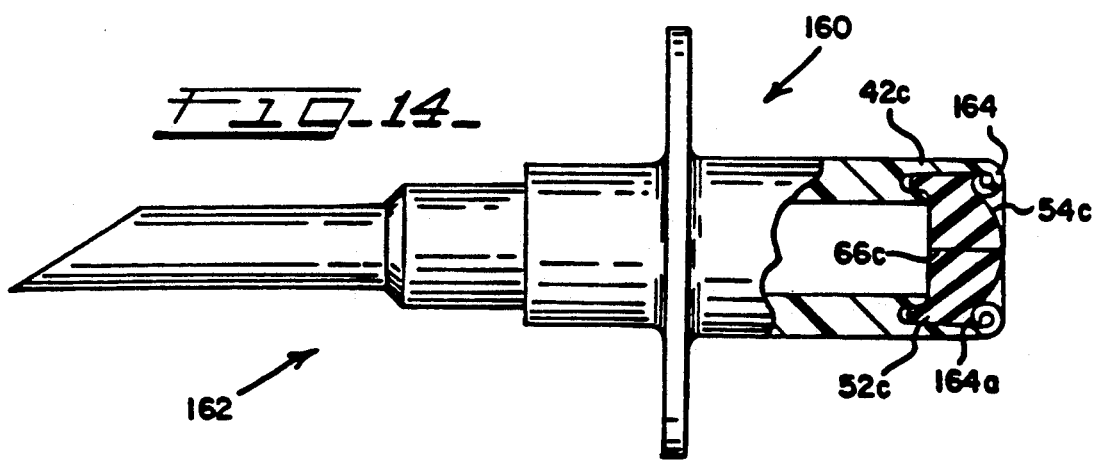

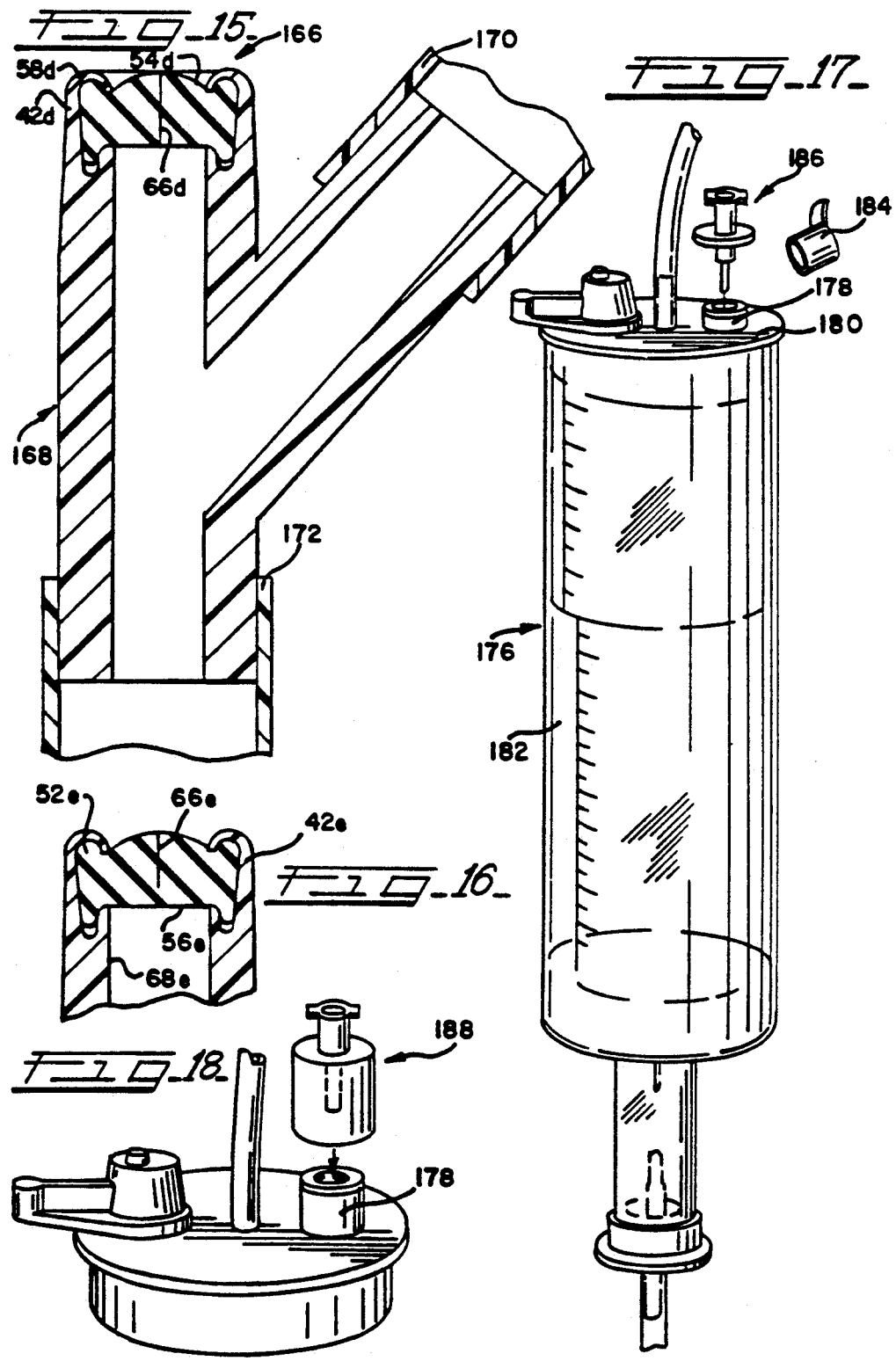

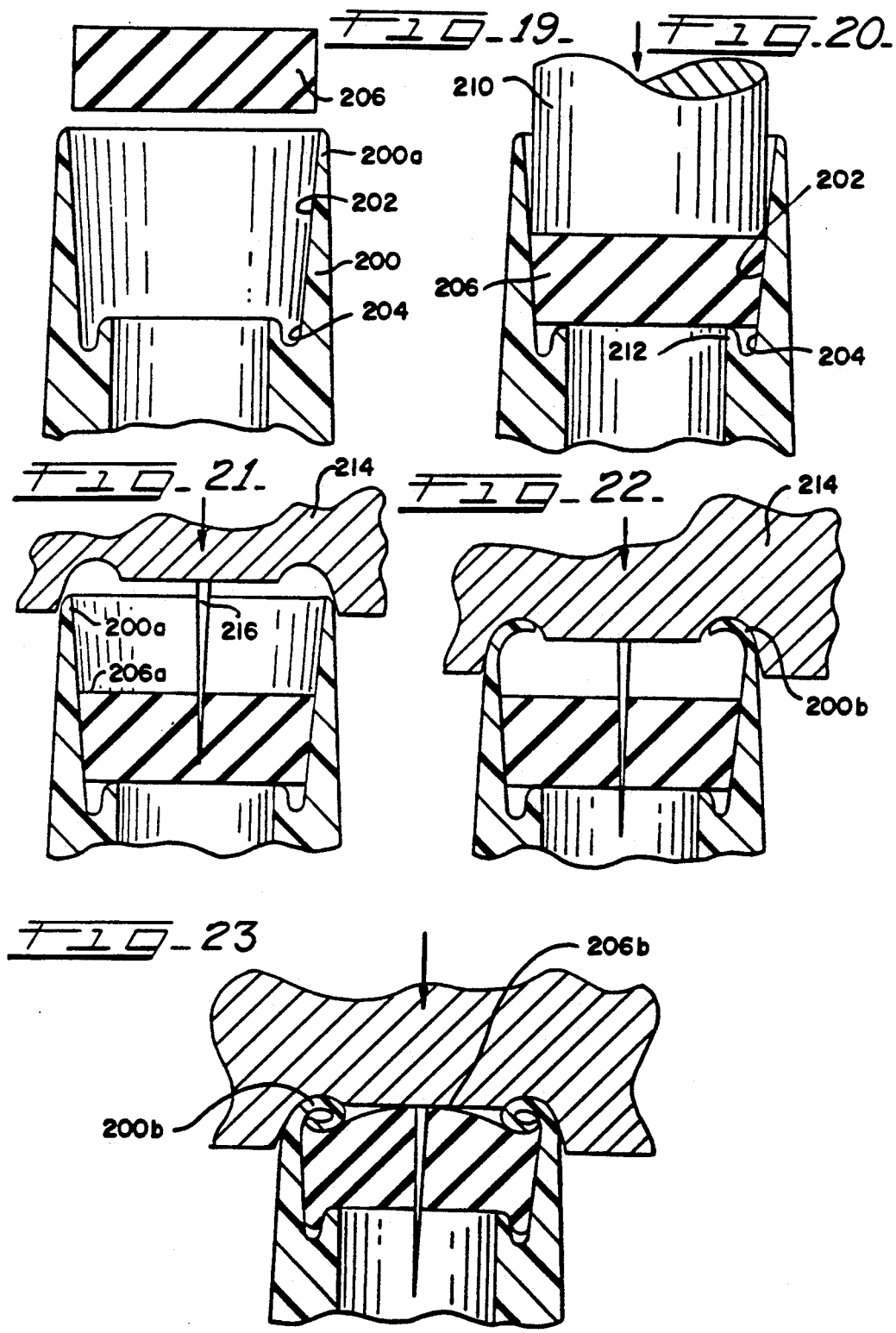

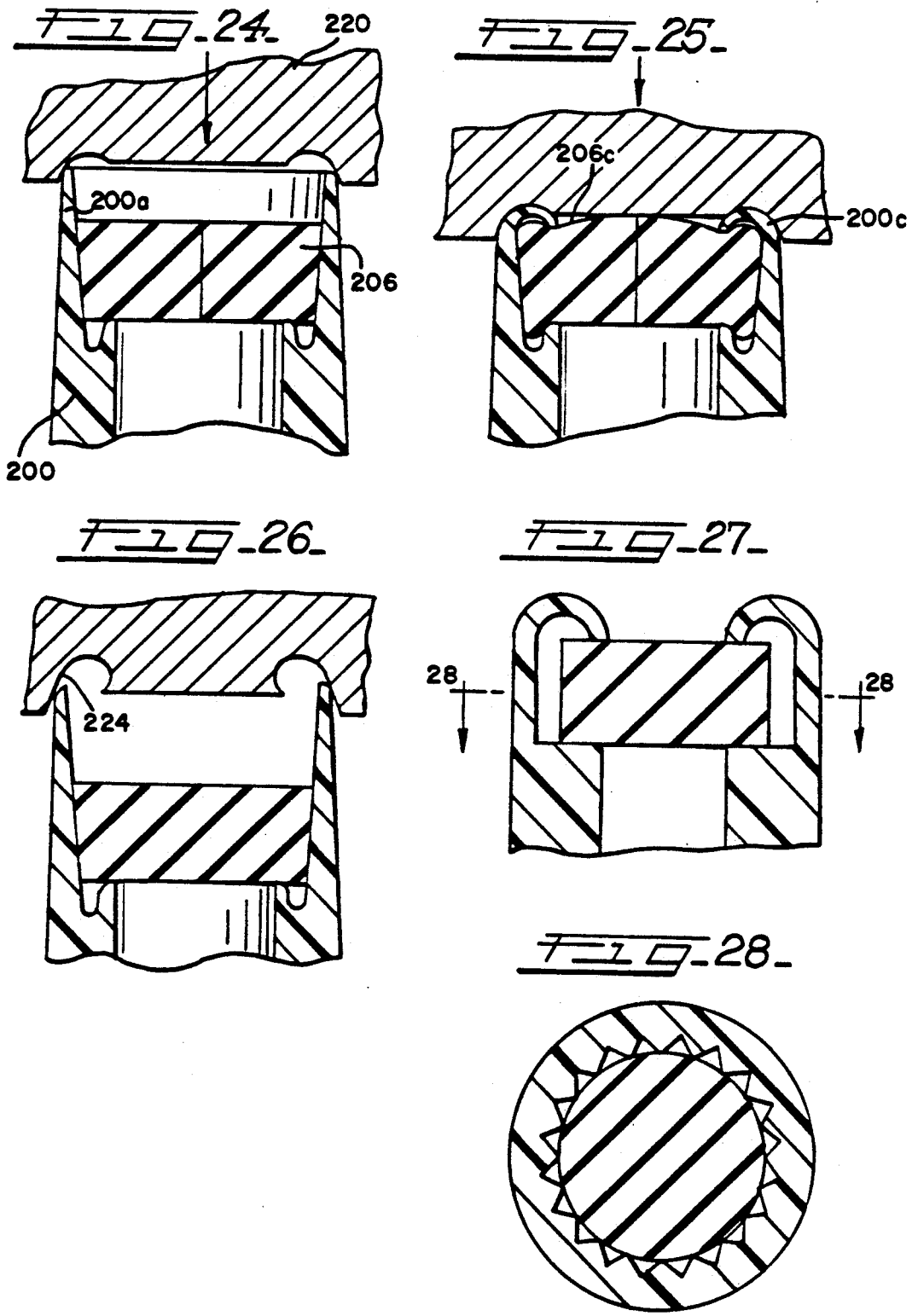

PRE-SLIT INJECTION SITE

CROSS-REFERENCE TO RELATED APPLICATION

This application is a continuation-in-part application of the co-pending and commonly assigned U.S. patent application, Ser. No. 147,414 entitled "Pre-Slit Injection Site And Associated Cannula" filed Jan. 25, 1988.

FIELD OF THE INVENTION

The invention pertains to coupling systems usable to transfer materials from one flow conduit to another. More particularly, the invention pertains to two-part coupling members with a first part including a pre-slit septum and a second part including a blunt cannula. The pre-slit septum slidably receives the blunt cannula to effect the coupling. The systems have particular applicability in the medical field for handling medications and body fluids.

BACKGROUND OF THE INVENTION

In the medical field, injection sites usable with pointed cannulae have long been known. For example, such sites can be formed with a housing having a fluid flow path therein. A septum is positioned in the housing closing the fluid flow path.

One injection site usable with a piercing cannula is disclosed in U.S. Pat. No. 4,412,573 to Zdeb entitled "Injection Site." The Zdeb patent is assigned to Assignee of the present invention.

The pointed cannula can be forced through the septum into fluid flow communication with the flow path in the housing. Known injection sites usable with a piercing cannula can be physically damaged by repetitive piercing caused by the sharp cannula. This damage, known as coring or laceration, can result in subsequent leakage.

For example, standard drug vials which have rubber stoppers or sites, are routinely entered with a conventional hypodermic needle. From repeated entry of the needle, the stopper may leak as a result of the coring and no longer function as a sterile barrier. Particulate matter can subsequently be generated and injected into the patient or otherwise contaminate the content of the vial. These problems are magnified with vials which are accessed multiple times.

Due to problems associated with infectious agents, Personnel using such pointed cannulae do so with great care. Notwithstanding careful and prudent practice, from time to time, accidents do occur and individuals using such pointed cannulae jab themselves.

In an effort to overcome some of these difficulties, devices known as "dispensing pins" can be used to penetrate the site or stopper of multiple dose vials. Such dispensing pins are typically a sharp spike cannula and can employ a check valve in an effort to prevent gross fluid leakage. On the opposing end of the cannula is a standard luer fitment typically closed off, when not in use, by a cap. These dispensing pins tend to disengage from the vial stopper so that some leakage still occurs. Further, it is difficult to maintain sterile conditions on this multiple dose system.

Injection sites usable with a blunt cannula are also known. For example, U.S. Pat. No. 4,197,848 issued to Garrett et al. entitled "Closed Urinary Irrigation Site" and assigned to the assignee of the present invention discloses one such injection site. That injection site is a relatively low pressure device having a relatively thin, molded, sealing member. The sealing member has an opening therethrough.

A blunt cannula can be forced through the sealing member placing the cannula into fluid flow communication with a fluid flow pathway in the injection site.

Injection sites of the type noted above usable with a blunt cannula have the advantage that the blunt cannula will not pierce the skin of a user. On the other hand, it is important that the pre-slit injection site reseal with enough force that fluids do not ooze therefrom and that airborne particulate matter, bacterial or viral matter do not enter therethrough.

Hence, there continues to be a need for a pre-slit injection site which can be used with a variety of solutions and over a range of fluid pressures. Further, there continues to be a need for such a pre-slit injection site which will reliably reseal even after many insertions of the blunt cannula.

Such an injection site should be able to receive a large number of insertions of the cannula without displaying reseal failure. Such an injection site should provide for improved alignment of the cannula on insertion. Improved alignment will result in less chance of damage to the injection site after repeated insertions of the cannula. Preferably, the injection site would also be usable with a pointed cannula. Preferably, a pre-slit injection site usable with a blunt cannula will provide a reasonable level of insertion force such that health care personnel w 11 readily be able to insert the blunt cannula, yet the cannula will not easily fall from or drop out of contact with the septum.

SUMMARY OF THE INVENTION

In accordance with the invention, an easily wipeable injection site usable with a blunt cannula is provided. The injection site includes a housing which defines a fluid flow channel therethrough. The housing has a first and a second end.

A flexible sealing member is carried by the housing for sealing the first end. The sealing member has a resealable opening therein. The sealing member also is formed with a curved exterior peripheral surface such that the blunt cannula can be sealingly inserted through the opening and placed in fluid flow communication with the flow path. Further, the blunt cannula can be removed from the opening with the sealing member then interacting with the housing so as to reseal the opening.

The housing can also be formed with the first end including an annular channel underlying the sealing member. The sealing member is subjected to radially directed forces by a tapered surface of the first end of the housing. These forces tend to reseal the opening in the sealing member.

The sealing member can be a cylindrically shaped rubber member. The first end of the housing can include an interior tapered surface for receiving the sealing member and for applying the radially directed forces to the sealing member.

A retaining member carried by the first end of the housing can be used to retain the sealing member with the housing. The retaining member can be generally U-shaped. Alternately, the retaining member can be formed as a coiled spring.

The retaining member applies axially directed forces to the sealing member. In one embodiment of the invention, the retaining member deflects the sealing member and forms a cured exterior peripheral surface thereon. The curved exterior peripheral surface is an easily wipeable surface.

The retaining member deflects or distorts the upper and lower peripheral edges slightly as a result of applying axial forces thereto. When the blunt cannula is inserted into the slit in the sealing member, an annular interior peripheral region of the sealing member deforms further and fills, at least in part, the annular channel.

Deformation of this annular peripheral region results in an insertion force in a range of 2.0 to 5 pounds. Preferably, the insertion force will have a value of the order of 2.0 pounds.

The resealable opening in the sealing member can extend entirely through that member. Alternately, the resealable opening can extend only partway therethrough. In this embodiment, the end of the blunt cannula will be used to tear through the remainder of the sealing member.

The sealing member can be formed in two parts. An exterior cylindrical portion can be slit completely. An interior cylindrical unslit portion can be provided to seal the site until the blunt cannula is inserted therethrough the first time.

The interior surface of the first end can be formed with the taper in a range on the order of 5 degrees to 20 degrees. Preferably, the interior surface will have a taper on the order of 12 degrees. This tapered surface permits the use of a cylindrically shaped sealing member.

To provide for leak-free insertion, the length of the slit in the sealing member must be less than one-half of the circumference of the cannula being inserted therethrough. Hence, the slit length may exceed the diameter of the cannula being inserted. In addition, the slit length must be great enough, given the elastic limit of the sealing member, to prevent tearing during insertion.

Further in accordance with the invention, a coupling system for coupling first and second fluid flow members together is provided. The coupling system includes an injection site which is affixed to the first fluid flow member. The injection site includes a housing. The housing has a fluid flow path therethrough.

A sealing member is carried by the housing. The sealing member has a resealable opening therein.

An annular retaining member is carried by the housing and cooperates with the housing to retain the sealing member therein. Radially directed forces are applied to the sealing member by the housing, thereby urging the opening into a resealed condition.

In further embodiments, the pre-slit injection site is usable with coupling components designed to adapt the injection site to standard vials or other conventional ports. The pre-slit injection site is combined with a vial adapter carrying an adapter spike in fluid flow communication with the flow path of the site. The adapter spike has openings which allow for the drainage of fluid in the vial through the spike and into the injection site. The vial adapter is provided with a skirt housing unit which protects the adapter spike in manufacturing and use. The skirt housing unit also provides features to lockingly engage the adapter with injection site with standard vials, despite dimensional variations in vial closures.

A blunt cannula, affixed to second fluid flow member, has a fluid flow path therethrough. The cannula engages the housing when the cannula extends through the opening of the sealing member. When so positioned, the two fluid flow members are placed into fluid flow communication.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 1 is a side elevational view, partly in section, of a prior art pre-slit injection site and an associated blunt cannula;

FIG. 2A is a view in perspective of a catheter positioned in the hand of a patient with a pre-slit injection site in accordance with the present invention positioned adjacent thereto;

FIG. 2B is a perspective view of the catheter of FIG. 2A with a pre-slit injection site in accordance with the present invention rotatably affixed thereto;

FIG. 3 is an enlarged side elevational view in section of a pre-slit injection site in accordance with the present invention formed on a body having a luer twist-lock type connector for coupling to a catheter;

FIG. 4A is an exploded view of a pre-slit injection site, a shielded blunt cannula and a syringe prior to being coupled together;

FIG. 4B is an enlarged, side elevational view in section of the pre-slit injection site, the shielded blunt cannula and the syringe of FIG. 4A coupled together to form a sealed fluid flow system;

FIG. 5A is a view in perspective of a pre-slit injection site prior to engaging a blunt cannula carrying a locking member;

FIG. 5B is an enlarged side elevational view, partly broken away, illustrating the interrelationship between the pre-slit injection site and the blunt cannula of FIG. 5A;

FIG. 6 is an overall view of a container, an associated solution administration set and a pre-slit injection site in accordance with the present invention;

FIG. 7 is an enlarged side elevational view, partly broken away illustrating the relationship between selected elements of FIG. 6;

FIG. 8 is a side elevational view, partly broken away illustrating an alternate shielded cannula in accordance with the present invention;

FIG. 9 is a side elevational view, partly in section, of a pre-slit injection site mounted on a fragment of a solution container;

FIG. 10 is a side elevational view of a fragment of a solution container carrying, as a single port, a pre-slit injection site;

FIG. 11 is a side elevational view of the injection site and the fragmentary container of FIG. 10 prior to being engaged with a shielded cannula carried by a syringe;

FIG. 12 is an enlarged side, elevational view, partly in section, of a coupling system with a pre-slit injection site partly coupled to a blunt cannula;

FIG. 13 is an enlarged side elevational view, partly in section, of the coupling system of FIG. 12 subsequent to engagement of the two coupling members;

FIG. 14 is a side elevational view, partly broken away, of a spike connector carrying a pre-slit injection site in accordance with the present invention;

FIG. 15 is an enlarged side elevational view of the Y-connector in section carrying a pre-slit injection site in accordance with the present invention;

FIG. 16 is an enlarged fragmentary side elevational view in section of a coupling member carrying a pre-slit injection site where the slit extends only partway through the septum;

FIG. 17 is a perspective view of a burette solution administration set carrying a pre-slit injection site in accordance with the present invention;

FIG. 18 is a view of part of a burette solution administration set carrying a pre-slit injection site being coupled to a shielded blunt cannula;

FIG. 19 is a step in the method of making a pre-slit injection site in accordance with the present invention;

FIG. 20 is another step in the method of making a pre-slit injection site in accordance with the present invention;

FIG. 21 is an initial phase of a final step in making a pre-slit injection site in accordance with the present invention;

FIG. 22 is an intermediate phase of the final step in a method of making a pre-slit injection site in accordance with the present invention;

FIG. 23 is a final phase of the final step in a method of making a pre-slit injection site in accordance with the present invention;

FIG. 24 illustrates an initial phase in an alternate step of making a pre-slit injection site in accordance with the present invention;

FIG. 25 illustrates a final phase of the alternate step in a method of making an injection site in accordance with the present invention;

FIG. 26 illustrates yet another alternate step in a method of making a pre-slit injection site in accordance with the present invention;

FIG. 27 is an enlarged, fragmentary cross-sectional view of another embodiment of an injection site in accordance with the present invention;

FIG. 28 is a cross-section view taken generally along the plane 28—28 in FIG. 27;

DETAILED DESCRIPTION OF A PREFERRED EMBODIMENT

Figure 29:
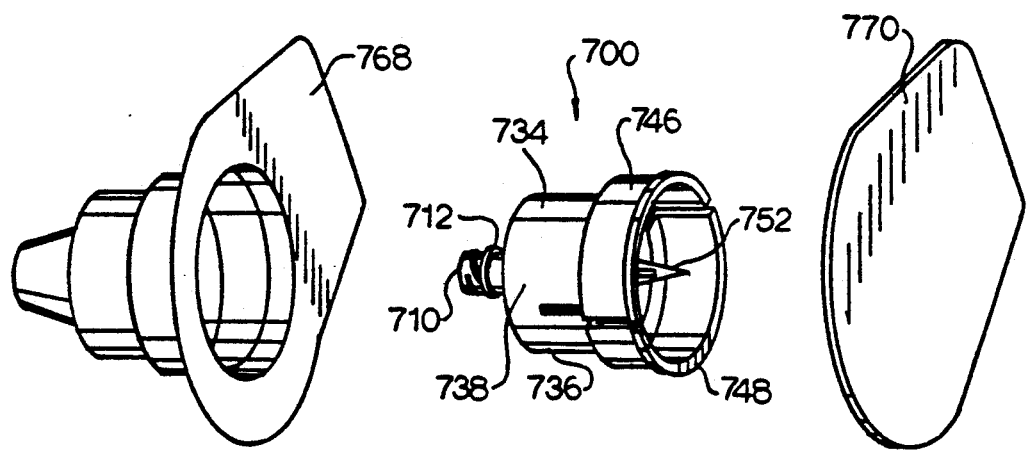
FIG. 29 is a perspective view of a single-use device packaging and a pre-slit injection site mounted on a vial adapter.
Figure 30:
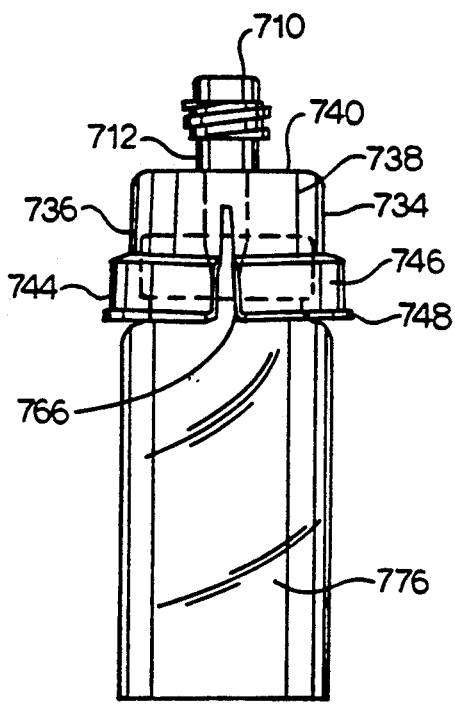
FIG. 30 is an elevational view of a pre-slit injection site mounted on a vial adapter as the adapter begins to engage a vial.

While this invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

A prior art pre-slit injection site 10 and associated blunt cannula 12 are illustrated in FIG. 1. The prior art injection site 10 has a cylindrical housing 14 with a fluid flow path 16 therethrough. A first end 18 of the housing 14 is closed with a relatively thin disc-shaped resealable member 20. The member 20 has a resealable opening 22 therein.

The member 20 is a molded septum with an integrally formed skirt 20a. The skirt 20a is oriented generally perpendicular to the portion of the septum with the opening 22.

The cannula 12 includes a body portion 24 which carries at a first end a hollow, cylindrical, blunt piercing member 26. As the cannula 12 is moved in a direction 28 toward the first end 18 of the injection site 10, the member 26 slidably engages the opening 22. The sealing member 20 is then deformed adjacent the opening 22 and the member 26 extends into the flow path 16. A fluid flow path through the cannula 12 will then be in fluid flow communication with the flow path 16 via the hollow piercing member 26.

In contradistinction to the prior art pre-slit injection site 10 of FIG. 1, FIGS. 2A and 2B illustrate a pre-slit injection site 34 being coupled to a peripheral venous catheter 36. The catheter 36 is shown in fluid flow communication with a vein in a hand H of a patient. The catheter 36 carries at a proximal end of catheter housing 38 a luer-type female twist lock connector 41.

The pre-slit injection site 34 is formed with a cylindrical housing 40 having a first end 42 and a second end 44. Carried by the housing 40 and adjacent to the second end 44 is a hollow cylindrical fluid flow member 46. The member 46 slidably engages a receiving member in the housing 38 of the catheter 36, thereby providing a sterile fluid flow coupling as is well known and conventional.

A plurality of the internal male luer-type threads 48 is carried by the housing 40 adjacent the second end 44. The threads 48 will engage the flange member 41 when the injection site 34 is rotated in a direction 50. When so coupled together, the catheter 36 and the injection site 40 provide a sealed coupling through which fluids may be injected into the vein of the hand H.

FIG. 3 illustrates, in section, further details of the injection site 34. A resealable septum 52 is carried by the first end 42 of the housing 40. The septum 52 includes first and second spaced apart surfaces 54 and 56 respectively. the surface 54 has been forced into a dome-like shape by annular, U-shaped, swaged end members 58 carried by the first end 42. The dome-like shape of the surface 54 can extend beyond a surface 42a of the first end 42. This facilitates cleaning the surface 54.

The septum 52 has a generally cylindrical shape. The septum 52 can be formed of a latex or synthetic rubber material. Alternately, the septum can be formed of a thermoplastic elastomer. The material used for the septum 52 should be non-toxic and sterilizable such as by means of radiation, steam or ethylene oxide.

Because the septum 52 is generally cylindrical in shape, it can be die-cut from a sheet, cut from an extruded rod or molded. The septum 52 can have an exemplary diameter on the order of 0.30 inches. The height of the septum 52 can be, for example, on the order of 0.125 inches.

The first end 42 is also formed with a tapered interior surface 60 which terminates in an annular channel 62. The tapered interior surface 60 has a taper in a range of 5 degrees to 20 degrees. Preferably, the taper will be on the order of 12 degrees. With the indicated size of the above noted exemplary septum 52 and a 12 degree taper, diametric resealing compression of the septum 52 adjacent the channel 62 is on the order of 10%.

The channel 62 is bounded in part by a septum supporting ridge 62a. The channel 62 can typically have a depth in a range of 0.050–0.070 inches.

A peripheral surface 64 of the septum 52 slidably engages the tapered interior surface 60 as the septum 52 slides into the first end 42. The annular channel 62 which underlies the interior peripheral surface 56 of the septum 52 is provided to permit the septum 52 to deform when a blunt cannula is inserted through an opening 66 therein.

The housing 40 is also formed with a fluid flow path 68 such that fluids injected via a blunt cannula inserted through the resealable opening 66 can flow into the catheter 36 for delivery to hand H of the patient.

The swaged end members 58 apply axial forces to the septum 52 thereby creating the domed exterior peripheral surface 54. The axial forces applied by the end members 58 slightly deform the regions 52a and 52b. In contradistinction, the tapered internal surface 60 applies radially directed forces to the septum 52, thereby forcing the opening 66 into a resealed condition.

In an alternate embodiment, the surface 52 could be formed as a flat, as opposed to a domed, surface.

Once the injection site 34 is lockingly engaged with the catheter 36, a sealed system is formed through which fluids can be infused into the catheter 36. The resealable septum 52 closes the fluid flow path 68.

FIGS. 4A and 4B illustrate in combination the injection site 34, a blunt shielded cannula 80 and a syringe of a conventional type 82. The syringe 82, as is well known, can be formed with a cylindrical hollow end 84 which carries a male luer-type twist lock thread 86. A hollow centrally located cylindrical fluid flow member 88 is in fluid flow communication with an interior region 90 of the syringe 82.

The shielded blunt cannula 80 carries at a first end 92 a female luer twist-lock flange 94. The flange 94 will slidably engage the threads 86 of the end 84. Hence, the shielded blunt cannula 80 can be locked to the syringe 82 forming a closed fluid flow pathway. The shielded cannula 80 could alternately be formed fixedly attached to the syringe 82.

The shielded blunt cannula 80 carries a cylindrical hollow protective shield 96 which surrounds a centrally located hollow, elongated cylindrical blunt piercing member 98. The cylindrical blunt piercing member 98 has a total length on the order of 3 times the thickness of the septum 52 in order to ensure complete penetration. The cylindrical blunt piercing member 98 has a diameter on the order of ½ the diameter of the septum 52. The shield 96 is desirable and useful for maintaining the piercing member 98 in an aseptic condition by preventing touch contamination prior to the shielded cannula 80 engaging the pre-slit septum 52. Also, the shield helps to align the piercing member with the pre-slit septum.

The cylindrical blunt piercing member 98 can slidably engage the pre-slit septum 52, best illustrated in FIG. 4B, thereby extending through the preformed opening 66 therein. As illustrated in FIG. 4B, when the piercing member 98 slidably engages and pierces the septum 52, the region 52a deforms by expanding into and filling, at least in part, the annular channel 62.

The deformation facilitates insertion of the piercing member 98 through the slit 66. Subsequent to the piercing member 98 slidably engaging the injection site 34, the interior region 90 of the syringe 82 is in fluid flow communication with the flow path 68 of the injection site 34 via flow paths 88a and 99 respectively of the syringe and the blunt piercing member 98.

In this engagement condition, the septum 52 seals completely around the piercing member 98. Hence, exterior gases, liquids or airborne matter will be excluded from the channel 68.

Subsequent to infusing fluid from the syringe 82 into the fluid flow pathway 68, hence into the catheter 36 and the hand H of the patient, the syringe 82 with lockingly engaged shielded cannula 80 can be slidably withdrawn from the injection site 34. Subsequent to this withdrawal, the septum 52 reseals the opening 66 therein.

The opening 66 will repeatedly reseal, when the piercing member 98 is removed, provided that the pressure (in the septum 52 of the opening 66) created by interaction of the septum material properties and compression supplied by the housing exceeds the pressure challenge of the fluid contained within. Blunt cannula do not haphazardly core, lacerate, or otherwise damage the sealing interface 66 as conventional needles do, thereby allowing repeatable resealability. However, septum material properties, thickness, and compression allow resealability for a finite number of conventional needle insertions. The combination injection site 34 and catheter 36 then return to its pre-infusion, sealed condition.

FIGS. 5A and 5B illustrate the pre-slit injection site 34 used in combination with a blunt cannula 80a. The cannula 80a includes piercing member 98a and manually operable elongated locking members 100a and 100b.

Curved end regions 100c of the members 100a and 100b slidably engage the second end 44 of the housing 40 when the piercing member 98 of the blunt cannula 80a has been forced through the pre-formed opening 66, best illustrated in FIG. 5B. The embodiment illustrated in FIGS. 5A and 5B has the advantage that the infusing cannula 80a cannot accidentally disengage from the pre-slit septum 34 during the fluid infusion process. It will be understood that while spring-like deflecting members 100a and 100b are illustrated in FIGS. 5A and 5B that other forms of locking members are within the spirit and scope of the present invention.

The blunt cannula 80a terminates at a proximal end with female luer fitting 94a. Alternately, a tubing member could be affixed to the hollow body portion 92a.

FIG. 6 illustrates an alternate pre-slit injection site 34a. A tubing member 102 can be fixedly attached to the cylindrical hollow fluid flow member 46. The embodiment 34a of FIG. 6 utilizes the same structure for the septum 52 including the tapered surface 60 and the underlying annular channel 62 as does the embodiment 34. The shielded cannula 80 can be utilized with the injection site 34a as previously described.

In the event that is desirable to infuse solution from a container 104 with a conventional port 106, a fluid administration set 110 of a conventional variety may be utilized. The set 110 includes a spike connection 112 at a first end. The spike connector 112 is designed to pierce the port 106 of the container 104. The set 110 can also carry a slidably engageable connector 114 of a known type at a second end. As illustrated in FIG. 7, the connector 114 can slidably engage the hollow cylindrical member 98 of the shielded cannula 80, thereby placing the interior fluid of the container 104 into fluid communication with the tubing member 102.

FIG. 8 illustrates yet another alternate 80b to the shielded cannula 80. The piercing member 98b carries a tubing member 118 fixedly attached thereto. The tubing member 118 could be coupled at a second end to a container such as the container 104.

The present pre-slit injection site can be directly affixed to a container 120 as illustrated in FIG. 9. The container 120 includes a rigid hollow cylindrical access port 122 affixed thereto. The access port 22 includes a fluid flow channel 124 in fluid flow communication with the interior of the container 120. Sealingly affixed to the port 122 is a pre-slit injection site 126.

The site 126 includes a cylindrical housing 128 which carries at a first end 130 a septum 32 with a slit 134 formed therein. The first end 130 has been swaged to form an annular U-shaped retaining member 136. The retaining member 136 in turn forms a domed exterior peripheral surface 138 on the septum 132.

The first end 130 also includes a tapered interior force applying surface 140 and an annular channel 142 underlying the septum 132. As discussed previously, the channel 142 provides a space into which the septum 132 can deform when a blunt cannula is forced through the resealable opening 134.

Further, as illustrated in FIG. 9, the injection site 126 can be covered by a removable cover 146 of a type used with the conventional port 16 of the bag 120.

While the bag 120 is illustrated formed with two ports, the conventional pierceable port 106 and the pre-slit injection site 126, it will be understood that as an alternate (FIG. 10), a container 150 could be formed which includes only the pre-slit injection port 126. The removable cover 146 could be used in combination with the container 150.

As illustrated in FIG. 11, the pre-slit injection site 126 can be utilized for the purpose of injecting fluid from the syringe 82, coupled to the shielded cannula 80, into the container 150. When so utilized, the blunt piercing member 98 is used to place the interior fluid containing region 90 of the interior of the container 150.

FIGS. 12 and 13 illustrate a fluid flow coupling system 151 having as a first element a pre-slit injection site 126a. The site 126a is the same as the site 126 except for a plurality of exterior threads 153 formed on an exterior peripheral surface 155 of the housing 128a. A second element of the coupling system 151 is formed as a shielded blunt cannula 157.

The shielded blunt cannula 157 is sealingly affixed to a flexible tubing member 159 by means of a proximal hollow cylindrical member 161. The member 144 extends into a hollow cylindrical shield 163 to form a blunt piercing member 165.

The shield 163 carries, on an interior peripheral surface, a set of coupling threads 149. The threads 149 match the threads 132.

The two connector elements 126a and 157 slidably engage one another when the shielded cannula 157 moves in an axial direction 167 toward injection site 126a. The blunt piercing member 165 penetrates the septum 132a.

The coupling member 157 can then be rotated in a direction 169 such the interior set of threads 149 carried thereon engages the exterior set of threads 153. As a result, the two coupling members 126a and 157 are lockingly engaged together with the insertion member 165 extending through the opening 134a in the septum 132a. Hence, fluids can flow from the container 150a via the connector system 126a and 157 through the tubing member 159 to the recipient.

Injection sites of the type described above are also usable in connection with other fluid flow coupling components. For example, with respect to FIG. 14, a pre-slit injection site 160 of the type described above can be used in combination with a spike connector 162 of a conventional variety. Spike connectors such as the spike connector 162 can be used to pierce conventional ports such as the port 106 of the container 104 (FIG. 6). When the spike connector 162 is so used, the pre-slit injection site 160 can then be utilized for the purpose of coupling to other fluid administration sets.

The injection site 160 illustrates an alternate form of swaging the first end 42c for the purpose of retaining the septum 52c therein. The first end 42c can be swaged so as to form an annularly shaped, spiral, spring-like member 164. The member 164 has a free end 164a which engages the exterior dome-shaped peripheral surface 4c of the septum 52. The spiral, spring-like swaged member 164 will tend to uncoil, thereby continuously applying axial force to the septum 52c and maintaining the domed exterior peripheral surface 54c.

In yet another alternate, FIG. 15 illustrates a pre-slit injection site 166 formed in a Y-junction member 168. The Y-junction member 168 is fixedly attached to first and second tubing members 170 and 172 respectively.

As an alternate to forming the slit 66 completely through the septum 52, as illustrated in FIG. 16 a slit 66e can be formed only partly through the septum 52e. such a structure has the further advantage that until used for the first time the septum 52e is completely sealed.

The septum 52 can be formed in two parts. One part can have a slit, such as the slit 66 extending entirely therethrough. A second part can be formed without a slit. These two parts can be located adjacent one another in first end 42 of the injection site.

The slit 66 may be longer on the top of the septum than
the bottom. This feature aids blunt cannula alignment with the slit upon insertion, and aids resealability by minimizing the critical slit sealing interface area.

In accordance with the present invention, the slit 66 could have a length with a range on the order of 0.03 to 0.150 inches. Preferably, a slit length in the order of 0.07 inches will be used in combination with a blunt cannula having a diameter on the order of 0.1 inches.

When initially used, the blunt cannula piercing member 98 will be forced through the slit 66a. The lower peripheral surface 56e will then be punctured, providing access for the blunt cannula piercing member 98 into the fluid flow pathway 68e.

Pre-slit injection sites of the type described above can be utilized in combination with burette solution administration sets. One such set 176 is illustrated in FIG. 17. The set 176 includes a pre-slit injection site 178 of the type described above. The injection site 178 is affixed to an exterior planar surface 180 of the burette 182. A removable cover 184 can be used to maintain the injection site 178 in an aseptic condition until blunt cannula 186 or 188 is inserted therethrough.

FIGS. 19-23 disclose a method of making a pre-slit injection site in accordance with the present invention. In a first step, a housing 200 is provided. The housing 200 has an interior tapered surface 202 at a first end 200a thereof. The interior peripheral surface terminates in an annular channel 204. A cylindrical septum 206 can be provided adjacent the end 200a.

In a second step, the septum 206 can be forced into the end 200c of the housing 200o and slightly deformed by the tapered peripheral surface 202 using an axially moving die 210. When positioned by the die 210, the septum 206 is located adjacent an internal annular ring 212 which bounds the annular channel 204.

In a third step, a second die 214 can be utilized to swag the end 200a into spiral-shaped, spring-like members 200b which apply axially directed forces against an exterior peripheral surface 206a of the septum 206. The axially directed forces form the flat surface 206a into a domed exterior peripheral surface 206b as illustrated in FIG. 23.

Simultaneously, with swaging the end members 200a so as to lock the septum 206 into the housing 200 and to form the domed exterior peripheral surface 206b, a knife 216 can be utilized to form a slit in the septum 206. Alternatively, the slit may be cut by a separate die in a separate step. If the septum 206 is formed as an extrusion, the slit can be created during the extrusion process. If the septum 206 is formed by stamping from a rubber sheet, the slit can be cut during the stamping process. If the septum 206 is formed by compression molding, the slit can be cut during the trimming process.

In order to extrude the slit into rod, a flat pin extrusion bushing can be used. A trailing ribbon may be attached to the bushing. The ribbon would prevent curing material across the slit. The ribbon or wire could be placed in the rod core and later stripped out leaving a slit. An inert substance, such as silicone oil, could be coextruded in the center of the rod to prevent curing across the slit and provide lubrication and a visible target for cannula insertion.

FIGS. 24 and 25 illustrates alternate swaging steps wherein a die 220 moving axially toward the housing 200 sages the end region 200a so as to form an annular U-shaped region 200c and the exterior domed peripheral surface 206c.

The dies 214 or 220 can be formed with various alternate shaped swaging surfaces 224, as illustrated in FIG. 26, depending on the precise shape of the end swage which is desired. It will be understood that all such variations in the swaging operation are within the spirit and scope of the present invention.

The injection site configuration need not be limited to the configurations depicted in FIGS. 3-5B, 9, 12-16. Rather, several configurations could be constructed without departing from the scope of this invention. Any such configuration would provide a flexible pre-slit sealing member captured in a housing which provides compression to create a seal against pressure and a void region accessible to the sealing member material only when displaced by a blunt cannula piercing member. One such possible configuration is depicted in FIGS. 27 and 28.

Another embodiment of a pre-slit injection site is illustrated in FIGS. 29-38. This embodiment 700 demonstrates the injection site of the type described above combined with a coupling component to permit the repeated access to a standard drug vial without using sharp needles. As in previously disclosed embodiments, a pre-slit injection site 710 is formed with a cylindrical housing 712 having a first end 714 and a second end 716. A resealable septum 718 is carried by first end 714 of housing 712. The septum 718 includes first and second spaced apart surfaces 720 and 722, respectively. The surface 720 has been forced into a dome-like shape by annular, U-shaped, swaged end members 724 carried by first end 714. The septum 718 is provided with a preformed opening 726. Carried by the housing 712 is a hollow fluid flow member 728 connecting the first end 714 and second end 716.

Figure 37:
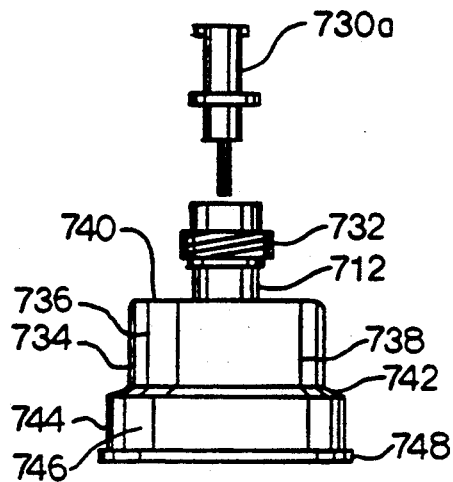
FIG. 37 is an elevational view of a pre-slit injection site mounted on a vial adapter being coupled to a blunt cannula in accordance with the present invention.
Figure 38:
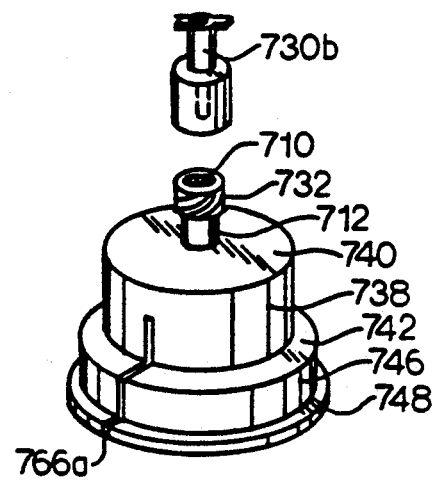
FIG. 38 is a perspective view of a pre-slit injection site mounted on a vial adapter being coupled to a blunt cannula with locking feature in accordance with the present invention.

As illustrated in FIGS. 37-38, threaded feature 732 is carried on the outside of the site housing 712 to readily receive and/or lockingly engage various embodiments of the blunt cannula such as those represented in FIGS. 37 and 38 as 730a and 730b, which have been previously described in co-pending parent application. To improve the engagement between the site and cannula, the threaded feature 732 may be provided with increased profiles and carry two nodes spaced 180° apart on the profiles. These increased profiles and nodes assist in compensating for normal dimensional tolerances in the blunt cannula.

The housing 712 of the pre-slit injection site 710 is combined with a coupling component or a vial adapter 736. Injection site 710 is molded onto a first skirt member 734 of vial adapter 736. The first skirt member 734 has a generally cylindrical wall 738 substantially closed on one end with a top member 740 of the vial adapter 736. The opposing portion of wall 738 is provided with a generally cylindrical step 742 which extends to connect with a second skirt member 744 of vial adapter 736. Having a larger diameter than first skirt member 734, second skirt 744 has a generally cylindrical wall 746 and terminates in a ridge 748.

Figures 34, 35:
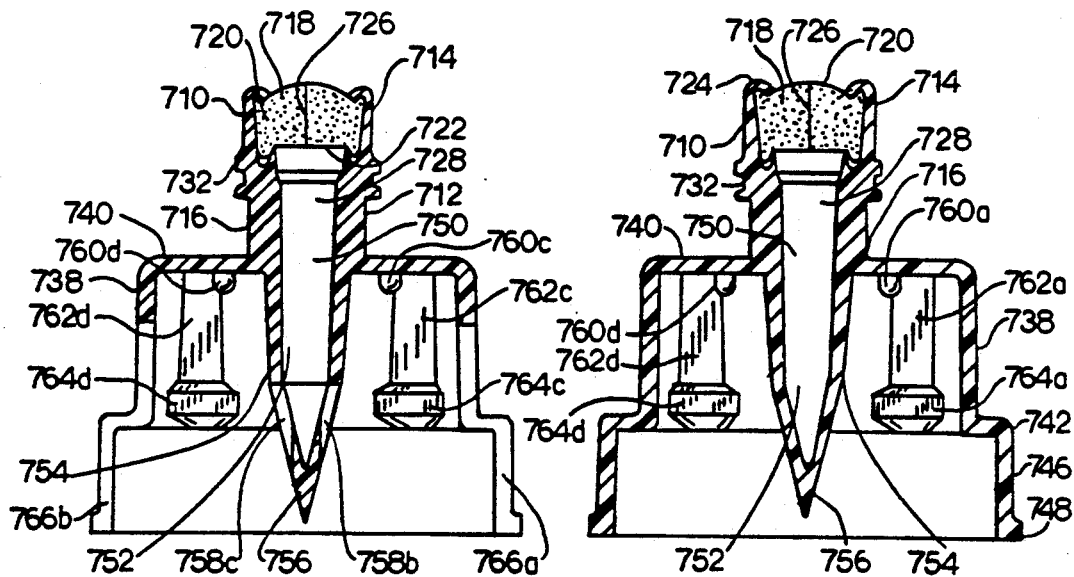
FIG. 34 is an enlarged side elevational view of a pre-slit injection site mounted on a vial adapter in section taken along line 34—34 of FIG. 32.
FIG. 35 is an enlarged side elevational view of a pre-slit injection site mounted on a vial adapter in section taken along line 35—35 of FIG. 32.

FIG. 34 illustrates, in section, the further details of the vial adapter 736 and the injection site 710. Generally centered in top member 740 is a hole 750 which is aligned with fluid flow member 728. In communication with fluid flow member 728, an adapter spike 752 is contiguous with hole 750. The adapter spike 752 has a generally cylindrical, hollow body portion 754 which tapers into a solid center point 756. The adapter spike 752 extends beyond the horizontal plane defined by step 742 but not beyond the horizontal plane defined by ridge 748. The second skirt 744 shields adapter spike 752 during the manufacturing and use of this embodiment of injection site 700.

Located in center point 756 is a bore 758. Embodiment 700 of pre-slit injection site and coupling component has preferably a bore formed of three peripheral openings 758a, 758b, 758c. Each opening extends from the joinder of body portion 754 and center point 756 and terminate prior to the opposing end of center point 756. With openings 758a–758c, a continuous flow passageway is established from injection site 710 through adapter spike 752.

As most clearly illustrated in FIGS. 33–36, the inner surface of top member 740 is provided with nib protrusions 760, preferably four protrusions, 760a–760d. Spaced evenly from one another, nib protrusions 760a–760d are positioned between the joinder of first skirt wall 738 with top member 740 and hole 750. Preferably aligned with nib protrusions 760a–760d are undercuts 762a–762d raised along the inner surface of first skirt wall 738. Each undercut 762a–762d terminates immediately adjacent to step 742 in a bump portion 764a–764d.

The vial adapter 736 is provided with preferably two slots, 766a and 766b located from ridge 748 through the skirts 734 and 744 terminating prior to top member 740.

This embodiment 700 of pre-slit injection site and coupling component can be packaged as a single-use medical device in a sterile rigid blister 768, adapted to temporarily contain device 700, and a peelable lid 770, as illustrated in FIG. 29. In application, a standard drug vial 776 having a vial closure 772 of aluminum carrying a rubber stopper 774 is prepared in accordance with the drug package. The device 700 is grasped through the package 768 and lid 770 is removed. Without direct contact between device 700 and the user, adapter spike 752 is positioned at the center of rubber stopper 774 and pressed firmly down towards vial 776 so that center point 756 pierces through stopper 774. To reduce the insertion force required, adapter spike 752 can be lubricated, for example, with silicone, prior to insertion of center point 756 into stopper 774.

By generally centering adapter spike 752 on stopper 774, second skirt member 744 is then permitted to pass over stopper 774 and surround vial closure 772 generally uninhibited. Slots 766a and 766b permit second skirt member 744 to expand so to slightly increase in diameter, compensating for dimensional variations among vial closures on standard drug vials.

Figure 36:
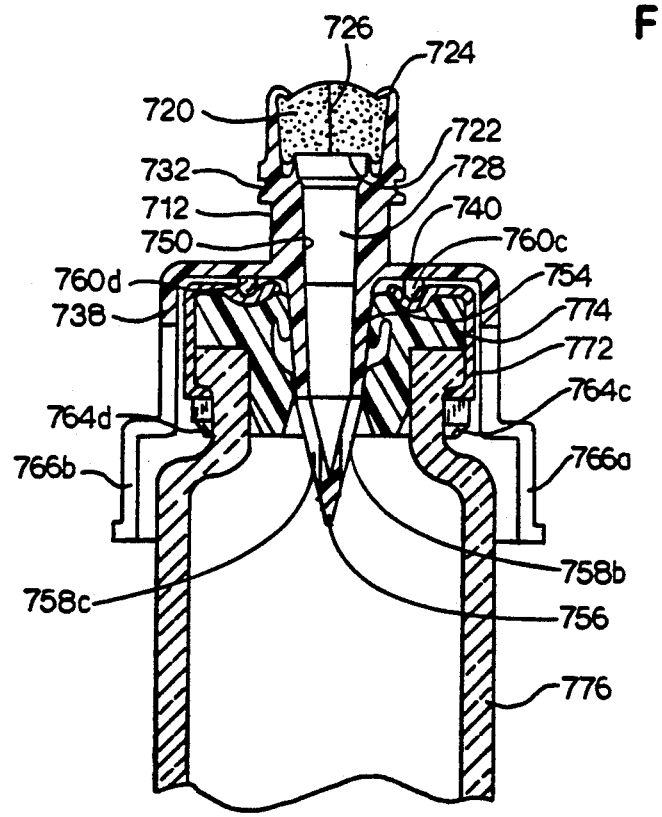
FIG. 36 is an enlarged cross sectional view of a pre-slit injection site mounted on a vial adapter lockingly engaged to a vial.

As adapter spike 752 continues through stopper 774, undercuts 762a–762d meet the top of vial closure 772 with resistance. Extending into first skirt member 734, slots 766a and 766b also permit the expansion of first skirt member 734 to assist in overcoming the initial resistance of undercuts 762a–762d. This initial resistance can then be overcome by a slight increase in insertion force as first skirt member 734 expands over vial closure 772. As the user continues to press device 700 into stopper 774, bump portions 764a–764d will each create indentations in the soft aluminum vial closure 772. Each undercut 762a–762d passes along the newly created indentations. As illustrated in FIG. 36, bump portions 764a–764d will come to rest in part under the lower edge of vial closure 772. In this position, bump portions 764a–764d provide resistance against device 700 from being disengaged from vial 776.

As bump portions 764a–764d are positioned under vial closure 772, top member 740 covers and, in some instances, may be in direct contact with the upper portion of vial closure 772 which carries stopper 774. Nib protrusions 760a–760d indent the aluminum upper portion of vial closure 772, preventing device 700 from rotating on vial 776.

Figure 31:
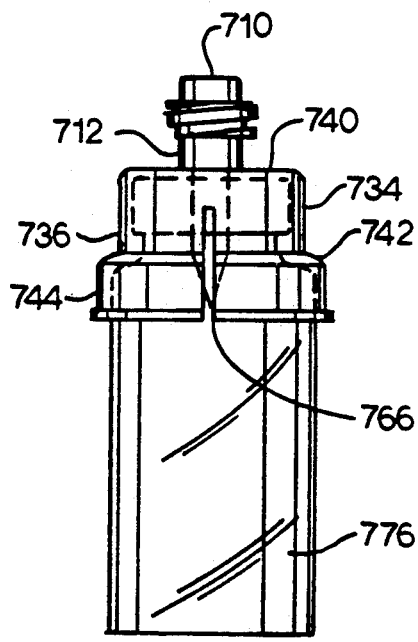
FIG. 31 is an elevational view of a pre-slit injection site mounted on a vial adapter lockingly engaged to a vial.
Figure 32:
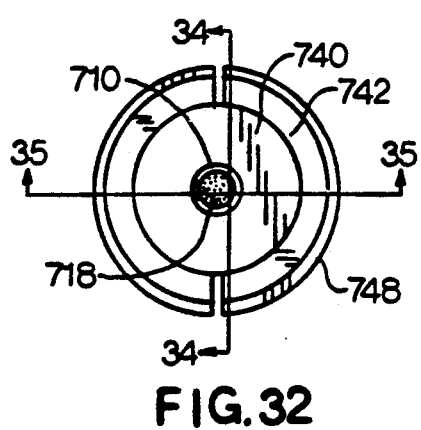
FIG. 32 is a top elevational view of a pre-slit injection site mounted on a vial adapter.
Figure 33:
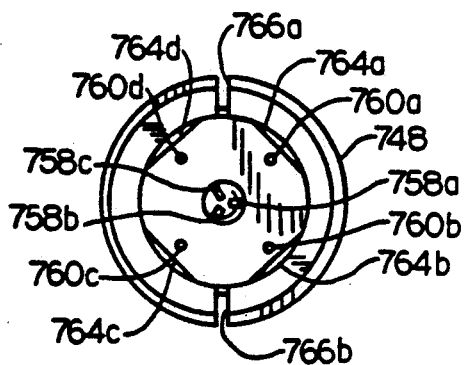
FIG. 33 is a bottom view of a pre-slit injection site mounted on a vial adapter.

Complete insertion of adapter spike 752 is achieved, as shown in FIGS. 31 and 36, when bump portions 764a–764d are engaged by the lower portion of closure 772 and nib protrusions 760a–760d indent the upper portion of closure 772. The undercuts 762a–762d are sized so that upon complete insertion of adapter spike 752, peripheral openings 758a–758c are inserted through stopper 774 and are completely within vial 776, permitting proper drainage of vial 776. After complete insertion, blister 768 can be separated from device 700 which is lockingly engaged with vial 776 in a sterile manner. The vial 776 can now be repeatedly accessed through device 700 by a blunt cannula as described in co-pending parent and continuation-in-part applications.

Figure 39:
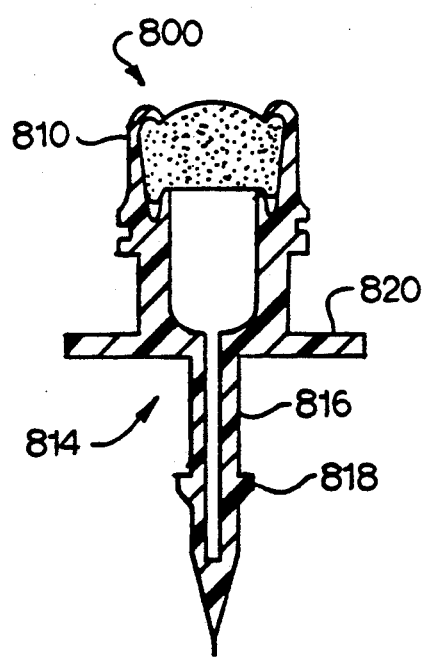
FIG. 39 is an enlarged cross sectional view of an embodiment of a pre-slit injection site in accordance with the present invention.

As illustrated in FIG. 39 as embodiment 800, injection sites of the type described are usable with yet another coupling component. Noted in co-pending application, Ser. No. 147,414, a pre-slit injection site 810 can be molded with a spike connector 814. In the embodiment described herein, the body 816 of the spike connector 814 can be provided with a barb feature 818. As with adapter spike 752, discussed above, spike connector 814 can be inserted through a vial stopper. Upon complete insertion, connector wall 820 between injection site housing 812 and spike body 816 will come to rest on the top of the vial closure. Further, barb feature 818 will be inserted through vial stopper and provide resistance against device 800 from being disengaged from the drug vial.

Figure 40:
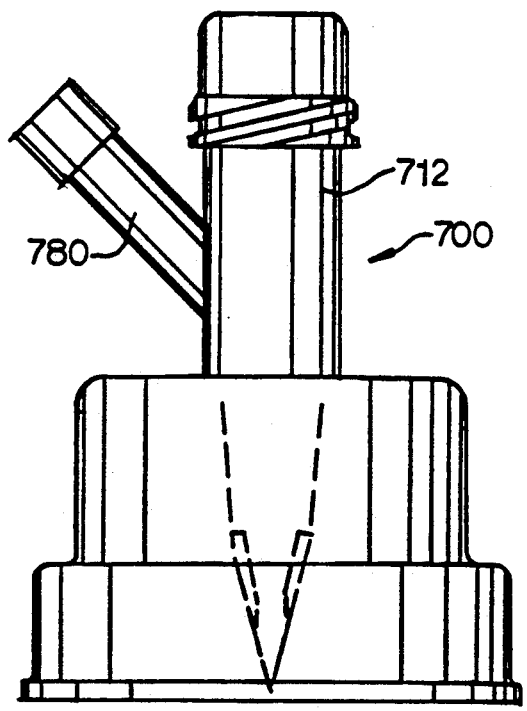
FIG. 40 is a perspective view of an embodiment of a pre-slit injection site mounted on a vial adapter in accordance with the present invention.

A further variation of device 700 described above, is shown in FIG. 40. As illustrated, the device 700 can be provided with a side arm 780 molded with site housing 712. Used as an air vent, side arm 780 can be provided with filters and valves well known in the art.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. An injection site usable with a blunt cannula comprising:
a housing defining a fluid flow channel therethrough, said housing having a first end and a second end;
a resilient sealing means, carried by said housing overlying said channel, for sealing said first end, said sealing means being formed with a resealable opening therein extending at least partway therethrough and an exterior peripheral surface;
a retaining means for retaining said sealing means in said housing such that a cannula can be sealingly inserted through said opening and placed in fluid flow communication with said flow channel and such that the cannula can be removed therefrom with said sealing means interacting with said retaining means to reseal said opening, said retaining means including a deformation of said housing first end against said exterior peripheral surface of said sealing means, said first end deformation applying axially directed forces to said sealing means;
a coupling component integral with said second end and continuing said fluid flow channel, said coupling component having a first skirt member, a second skirt member, and a step member extending between and connecting said skirt members;

a spike having a bore and carried by said first skirt member, extending in a space relation from the skirt members beyond a horizontal plane defined by the step member; and, a connector means for lockingly engaging said site to a vial such that said spike can be inserted into said vial and provide drainage of the vial fluid through said fluid flow channel.

2. An injection site as in claim 1 wherein said first skirt member comprises a generally cylindrical wall having at one end a top member defining a hole and at the opposing end said step is contiguous with said second skirt member.

3. An injection site as in claim 1 wherein said first and second skirt members carry a slot member.

4. An injection site as in claim 1 wherein said spike comprises a substantially cylindrical, hollow body portion tapering to a solid center point.

5. An injection site as in claim 4 wherein said bore includes three peripheral openings carried between said body and said center point.

6. An injection site as in claim 1 wherein said connector means includes undercut members carried by said first skirt member for engagement with a vial closure.

7. An injection site as in claim 1 wherein said connector means includes protrusion members carried by said first skirt member for engagement with a vial closure.

8. An injection site as in claim 1 with said housing carrying threaded connecting means having node members.

9. An injection site as in claim 1 wherein said housing includes an air vent.

10. An injection site usable with a blunt cannula comprising:

a housing defining a fluid flow channel therethrough, the housing having a first end and a second end;

a resilient sealing means, carried by the housing overlying the channel, for sealing the first end, the sealing means being formed with a resealable opening therein extending at least partway therethrough and an exterior peripheral surface;

a retaining means for retaining the sealing means in the housing such that a cannula can be sealingly inserted through the opening and placed in fluid flow communication with the flow channel and such that a cannula can be removed therefrom with the sealing means interacting with the retaining means to reseal the opening, the retaining means including a deformation of the housing first end against the exterior peripheral surface of the sealing means, the first end deformation applying axially directed forces to the sealing means;

a coupling component integral with the second end and continuing the fluid flow channel, the coupling component having a first skirt member with a generally cylindrical wall and at one end a top member defining a hole adaptable to receiving the second end, a second skirt member, and a step member extending between and connecting the skirt members;

a spike carried by the first skirt member, extending in a space relation from the skirt members beyond a horizontal plane defined by the step member, the spike having a bore with a substantially cylindrical, hollow body portion tapering to a solid center point and at least one peripheral opening positioned between the body and the center point; and, a connector means for lockingly engaging the site to a vial such that the spike can be inserted into the vial and provide drainage of the vial fluid through said fluid flow channel, the connector means including a slot member and at least one undercut member carried by the first skirt member for engagement with a vial closure.

11. An injection site usable with a blunt cannula comprising:

a housing defining a fluid flow channel therethrough, the housing having a first end and a second end;

a resilient sealing means, carried by the housing overlying the channel, for sealing the first end, the sealing means being formed with a resealable opening therein extending at least partway therethrough and an exterior peripheral surface;

a retaining means for retaining the sealing means in the housing such that a cannula can be sealingly inserted through the opening and placed in fluid flow communication with the flow channel and such that a cannula can be removed therefrom with the sealing means interacting with the retaining means to reseal the opening, the retaining means including a deformation of the housing first end against the exterior peripheral surface of the sealing means, the first end deformation applying axially directed forces to the sealing means;

a coupling component integral with the second end and continuing the fluid flow channel, the coupling component having a first skirt member with a generally cylindrical wall and at one end a second skirt member, and a step member extending between and connecting the skirt members;

a spike carried by the first skirt member, extending in a space relation from the skirt members beyond a horizontal plane defined by the step member, the spike having a bore with a substantially cylindrical, hollow body portion tapering to a solid center point and at least one peripheral opening positioned between the body and the center point; and, a connector means for lockingly engaging the site to a vial such that the spike can be inserted into the vial and provide drainage of the vial fluid through said fluid flow channel, the connector means including a slot member, at least one undercut member and at least one protrusion member, both the undercut member and protrusion member being carried by the first skirt member for engagement with a vial closure.

* * * * *

UNITED STATES PATENT AND TRADEMARK OFFICE
CERTIFICATE OF CORRECTION

PATENT NO.   :   5,100,394
DATED        :   March 31, 1992
INVENTOR(S)  :   Thomas E. Dudar et al.

It is certified that error appears in the above-identified patent and that said Letters Patent is hereby corrected as shown below:

In column 2, line 31, the text reads, "w ll readily..."; it should correctly read ---will readily....

In column 6, line 2, after the word invention there is a colon ":" where there should be a semicolon ---;--- instead.

In column 6, line 32, the text reads, "ho low. cylindrical."; it should correctly read ---hollow, cylindrical....

In column 16, line 41, a line of typing has been omitted. After the words "at one end", the following should be inserted:   ---a top member defining a hole adaptable to receiving the second end,---.

Signed and Sealed this

Twenty-second Day of June, 1993

Attest:

MICHAEL K. KIRK

*Attesting Officer*     Acting Commissioner of Patents and Trademarks